(12) United States Patent
Kodama et al.

(10) Patent No.: US 6,473,641 B1
(45) Date of Patent: Oct. 29, 2002

(54) BIOELECTRIC IMPEDANCE MEASURING APPARATUS

(75) Inventors: Masato Kodama, Tokyo (JP); Yoshikazu Yoshida, Tokyo (JP)

(73) Assignee: Tanita Corporation, Tokyo (JP)

( * ) Notice: Subject to any disclaimer, the term of this patent is extended or adjusted under 35 U.S.C. 154(b) by 78 days.

(21) Appl. No.: 09/672,899

(22) Filed: Sep. 29, 2000

(30) Foreign Application Priority Data

Sep. 30, 1999 (JP) ............................................ 11-278662
Jul. 26, 2000 (JP) ........................................ 2000-224944

(51) Int. Cl.$^7$ ................................................. A61B 5/05
(52) U.S. Cl. ...................................................... 600/547
(58) Field of Search ................................. 600/547, 300; 607/66; 128/897, 898

(56) References Cited

U.S. PATENT DOCUMENTS 3,821,949 A * 7/1974 Hartzell et al. ............. 600/547
5,307,817 A * 5/1994 Guggenbuhl et al. ....... 600/547
5,746,214 A * 5/1998 Brown et al. ............... 600/547
6,321,119 B1 * 11/2001 Kronberg .................... 607/66
6,336,045 B1 * 1/2002 Brooks ........................ 600/547

FOREIGN PATENT DOCUMENTS

JP          10-01498          1/1998

* cited by examiner

Primary Examiner—Kevin Shaver
Assistant Examiner—Brian Szmal
(74) Attorney, Agent, or Firm—McDermott, Will & Emery

(57) ABSTRACT

Disclosed is a bioelectric impedance measuring apparatus which can prevent such abnormal condition than an excessive current is applied to a human body when elements in the circuit has failed or is damaged, with a simple circuit configuration and without decreasing the measuring accuracy of the bioelectric impedance. The bioelectric impedance measuring apparatus according to the present invention is configured such that a capacitor or a set of a capacitor and a resistor arranged in parallel with each other is installed between an electrode to be brought into contact with a human body and a bioelectric impedance measuring circuit section comprising a generating section for generating an alternating current applied to a human body for measurement, a measuring section for measuring a voltage value between the portions where the current is applied to the human body, a computing section for computing a bioelectric impedance value, and a central processing unit (CPU).

7 Claims, 5 Drawing Sheets

FIG. 1

| CURRENT | CATEGORY | EFFECT ON HUMAN BODY |
|---------|----------|----------------------|
| 1mA | LEAST SENSING CURRENT | SLIGHT PAIN |
| 5mA | SENSING CURRENT | CONSIDERABLE PAIN |
| 10mA | ESCAPING CURRENT | CONSIDERABLE PAIN, STILL ABLE TO EXERCISE MUSCLES FREELY |
| 20mA | | MUSCLES BECOME NUMB, LIMIT OF ESCAPING BY ONESELF |

BIOELECTRIC IMPEDANCE MEASURING APPARATUS

BACKGROUND OF THE INVENTION

1. Field of the Invention

The present invention relates to an impedance measuring apparatus for measuring based on a bioelectric impedance method a body constitution such as a body fat rate representing a rate of fat weight to total human body weight, a body fat mass representing an absolute weight value of the fat, or a total body water volume, and, in particular, to a safety countermeasure for preventing an element of the measuring apparatus from making an undesirable effect on a human body when a circuit element in the measuring apparatus has failed.

2. Description of the Prior Art

Conventionally, it has been known that the body constitution can be estimated by measuring a bioelectric impedance, as described in The American Journal of Clinical Nutrition, 41(4) 810–817 1985 "Assessment of fat-free mass using bioelectrical impedance measurement of the human body". As for a method for measuring body fat mass contained in a human body by employing this mechanism, there has been known a method for measuring body fat mass in which an impedance between body ends such as hands and feet is measured by a four terminal electrode method and the body fat mass is determined by combining the measured impedance value with personal body information such as weight, height, sex, age, etc., and further an apparatus for measuring the weight of a person to be measured together with the body fat mass simultaneously is disclosed by the Japanese Patent Publication No. Hei 5-49050. Various apparatuses employing this mechanism have already spread in market.

These conventional body fat meters are generally configured as shown in FIG. 5 of the accompanying drawings.

FIG. 5 is a block diagram briefly illustrating a configuration of a general body fat meter employing the bioelectric impedance method. The body ends of a person to be measured, or a right and a left hands or feet are brought into contact with current electrodes 72A, 72B and voltage electrodes 73A, 73B. When a measurement start switch in a switch group 87 is pressed, a measuring current or an alternating current of about 50 kHz and of about 500 µA is generated by a current supply section 81 in response to a signal from a CPU 80. This alternating current is the measuring current and is applied through the current electrodes 72A, 72B to the body of a person to be measured, and then a voltage value between the voltage electrodes 73A, 73B is detected by a voltage detecting section 82, and thereby a bioelectric impedance value is determined. A body fat rate or a body fat mass is estimated based on preset body information of the person to be measured and the determined bioelectric impedance value, and the result thereof is displayed on a display circuit 88. The current supply section 81 and the voltage detecting section 82 to which these electrodes 72A, 72B, 73A, and 73B are connected are composed of a plurality of electronic components such as amplifiers (operational amplifiers), resistors, and capacitors.

A battery 89 is connected to a constant voltage supply section 90, where a rated voltage (Vdd and −Vdd) is generated and output to drive the overall measuring circuit, that is, the constant voltage supply section 90 is connected to respective ICs including CPU 80 to supply a constant voltage. This constant voltage supply section 90 generally employs a three terminal regulator or the like.

As described above, the body fat meter according to the bioelectric impedance method is configured such that electrodes are directly brought into contact with the skin of the person to be measured and the body fat rate and the body fat mass are measured by actually applying a small alternating current to a human body during the measurement.

However, since various electronic components are employed in the current supply section 81 and the voltage detecting section 82 as described above, and these electronic components are precisely configured, they are likely to fail if these circuits and components are subjected to such loads as static electricity, high temperature, or the like, and further the terminals of these electronic components may be separated from the substrate if the body fat meter is dropped. In such cases, the current cannot be correctly controlled, and subsequently a current greater than expected may possibly be applied to the human body through the respective electrodes 72A, 72B, 73A, and 73B.

Since a human being is a creature having a sensory organ, applying a current greater than a certain level to the body may cause a person to feel numbness or pain. FIG. 1 of the accompanying drawings is a table showing the current effect on a human body, classified by a category and a level of the current. This table indicates that a human body begins to sense a current and to react thereto when a current greater than 1 mA is applied. As the current increases, the initial slight pain turns into a strong pain. A current of about 20 mA is regarded as a limit current, which a human being can endure and from which he or she can escape by himself or herself.

Since FIG. 1 shows a case for an adult male with a current applied for one second, similar conditions for females and children may be observed at considerably lower currents than these values.

As described above, when an excessive current greater than a certain level is applied to a human body, the body is subjected to a heavy load. Accordingly, an electric instrument is desired to be equipped with a safety countermeasure for preventing a negative effects caused thereby, and especially in a body fat meter which determines a bioelectric impedance value by applying a current to the human body, an improvement is desired from the viewpoint of electrical safety.

For this safety countermeasure, it is generally contemplated as one method that the measuring current applied to the human body is continuously detected and the circuit power supply is turned off when the current exceeds a specified level. Further, it is contemplated as an alternative method that the measuring current is limited by adding a high resistor between a measuring circuit section and an electrode plate.

Although several safety countermeasures including those described above can be contemplated to prevent an abnormal current from being applied to the human body when a circuit element of a body fat meter employing the bioelectric impedance method has failed or a life thereof has run out, the one method described above to turn off the power supply in case of a current greater than a specified level being applied makes the circuit configuration of the overall measuring apparatus complicated and demands more components, which results in the cost increase of the apparatus.

Though the circuit configuration is simple in the alternative method described above which employs a high resistor installed between the measuring circuit and the electrode, the circuit for measuring the bioelectric impedance has a higher resistance than the impedance of the human body, and this has negative effects on measurement errors, and finally results in a decreased accuracy in measuring the body fat rate and the body fat mass.

The present invention is made in the light of these problems described above and the object thereof is to provide a safety countermeasure against an abnormal condition which may be caused by an excessive current applied to the human body when the element has failed or broken, using a simple circuit configuration without decreasing the accuracy in measuring the bioelectric impedance, and also to provide a bioelectric impedance measuring apparatus equipped with a safety countermeasure enabling an estimation of an index relating to body constitution such as body fat mass, total body water volume.

SUMMARY OF THE INVENTION

According to an aspect of the present invention, there is provided a bioelectric impedance measuring apparatus which has a plurality of electrodes to be brought into contact with the skin of a person to be measured, a measuring circuit section which is connected to said plurality of electrodes and applies an alternating current to the body of the person and measures the bioelectric impedance, determines a bioelectric impedance value based on the bioelectric impedance analysis and estimates an index regarding the body constitution of the person, said apparatus characterized in that a set of a capacitor and a resistor arranged parallel with each other is installed between each of said electrodes and said measuring circuit section.

According to another aspect of the present invention, there is provided a bioelectric impedance measuring apparatus which has a plurality of electrodes to be brought into contact with the skin of a person to be measured, a measuring circuit section which is connected to said plurality of electrodes and applies an alternating current to the body of the person and measures the bioelectric impedance, determines a bioelectric impedance value based on the bioelectric impedance analysis and estimates an index regarding the body constitution of the person, said apparatus characterized in that at least one set of a capacitor and a resistor arranged parallel with each other is installed between said electrodes and said measuring circuit section.

According to another aspect of the present invention, there is provided a bioelectric impedance measuring apparatus which has a plurality of electrodes to be brought into contact with the skin of a person to be measured, applies an alternating current to the body of the person, a current supply circuit and a voltage measuring circuit which is connected to a plurality of electrodes, determines a bioelectric impedance value based on the bioelectric impedance analysis and estimates an index regarding the body constitution of the person, said apparatus characterized in that a set of a capacitor and a resistor arranged parallel with each other is installed between each of voltage measuring electrode among said electrodes and said voltage measuring circuit.

According to another aspect of the present invention, there is provided a bioelectric impedance measuring apparatus which has a plurality of electrodes to be brought into contact with the skin of a person to be measured, applies an alternating current to the body of the person, a current supply circuit and a voltage measuring circuit which is connected to a plurality of electrodes, determines a bioelectric impedance value based on the bioelectric impedance analysis and estimates an index regarding the body constitution of the person, said apparatus characterized in that a set of a capacitor and a resistor arranged parallel with each other is installed between at least one voltage measuring electrode among said electrodes and said voltage measuring circuit.

According to another aspect of the present invention, there is provided a bioelectric impedance measuring apparatus which has a plurality of electrodes to be brought into contact with the skin of a person to be measured, applies an alternating current to the body of the person, a current supply circuit and a voltage measuring circuit which is connected to a plurality of electrodes, determines a bioelectric impedance value based on the bioelectric impedance analysis and estimates an index regarding the body constitution of the person, said apparatus characterized in that a set of a capacitor and a resistor arranged parallel with each other is installed between each of current supply electrodes among said electrodes and said current supply circuit.

According to another aspect of the present invention, there is provided a bioelectric impedance measuring apparatus which has a plurality of electrodes to be brought into contact with the skin of a person to be measured, applies an alternating current to the body of the person, a current supply circuit and a voltage measuring circuit which is connected to a plurality of electrodes, determines a bioelectric impedance value based on the bioelectric impedance analysis and estimates an index regarding the body constitution of the person, said apparatus characterized in that a set of a capacitor and a resistor arranged parallel with each other is installed between at least one current supply electrode among said electrodes and said current supply circuit.

According to an embodiment of the present invention, a set of a capacitor and a resistor arranged parallel with each other is further installed between each of voltage measuring electrodes among said electrodes and said voltage measuring circuit.

According to another aspect of the present invention, there is provided a bioelectric impedance measuring apparatus which has a plurality of electrodes to be brought into contact with the skin of a person to be measured, a measuring circuit section which is connected to said plurality of electrodes and applies an alternating current to the body of the person and measures the bioelectric impedance, determines a bioelectric impedance value based on the bioelectric impedance analysis and estimates an index regarding the body constitution of the person, said apparatus characterized in that between each of said electrodes and said measuring circuit section, a capacitor is installed close to said electrode and a diode for electrostatic safety countermeasure is installed close to said measuring circuit.

According to another aspect of the present invention, there is provided a bioelectric impedance measuring apparatus which has a plurality of electrodes to be brought into contact with the skin of a person to be measured, a measuring circuit section which is connected to said plurality of electrodes and applies an alternating current to the body of the person and measures the bioelectric impedance, determines a bioelectric impedance value based on the bioelectric impedance analysis and estimates an index regarding the body constitution of the person, said apparatus characterized in that between each of said electrodes and said measuring circuit section, a set of a capacitor and a resistor arranged parallel with each other is installed close to said electrode and a diode for electrostatic safety countermeasure is installed close to said measuring circuit.

According to an embodiment of the present invention, the said capacitor is a ceramic capacitor.

There will now be described in detail preferred embodiment of the present invention with reference to the drawings.

BRIEF DESCRIPTION OF THE DRAWINGS

FIG. 1 is a table illustrating an effect of a current applied to the human body;

DESCRIPTION OF THE PREFERRED EMBODIMENTS

A bioelectric impedance measuring apparatus according to the present invention is configured such that a capacitor or asset of a capacitor and a resistor arranged parallel with each other is installed between an electrode to be brought into contact with a human body and a bioelectric impedance measuring circuit section comprising a generating means for generating an alternating current applied to a human body for measurement, a measuring means for measuring a voltage value between portions where said current is applied to the human body, a computing means for computing a bioelectric impedance value, and a central processing unit (CPU) for controlling and processing said means.

A capacitor acts as an impedance element in an electric circuit and has an infinite resistance when direct current energy is to be transferred and has a smaller resistance as the alternating current frequency increases. A capacitor can constitute various kinds of transmission circuits for electric energy when combined with a resistor having an impedance which is not dependent on frequency and an inductance having an impedance whose frequency characteristic is reverse to that of a capacitor. No detailed description will be made further since this is well known and described in various reference books on electric circuits, but it should be noted that no current passes through a capacitor when the current frequency "f" is 0 Hz, that is, the current is a direct current. Accordingly, in an embodiment of the present invention, only an alternating current can be applied to the body of the person to be measured, and no direct current can be applied. This can prevent a direct current greater than a specified value from being applied to the human body even if electronic components of the measuring circuit section have failed. The term of "measuring circuit section" of the present invention is used as a general term which includes not only a limited portion of a voltage measuring circuit but also the overall elements including a current supply section and a voltage detecting section necessary for measuring the bioelectric impedance.

Preferred embodiments of the present invention will be described in detail with reference to the attached drawings.

Figure 2:
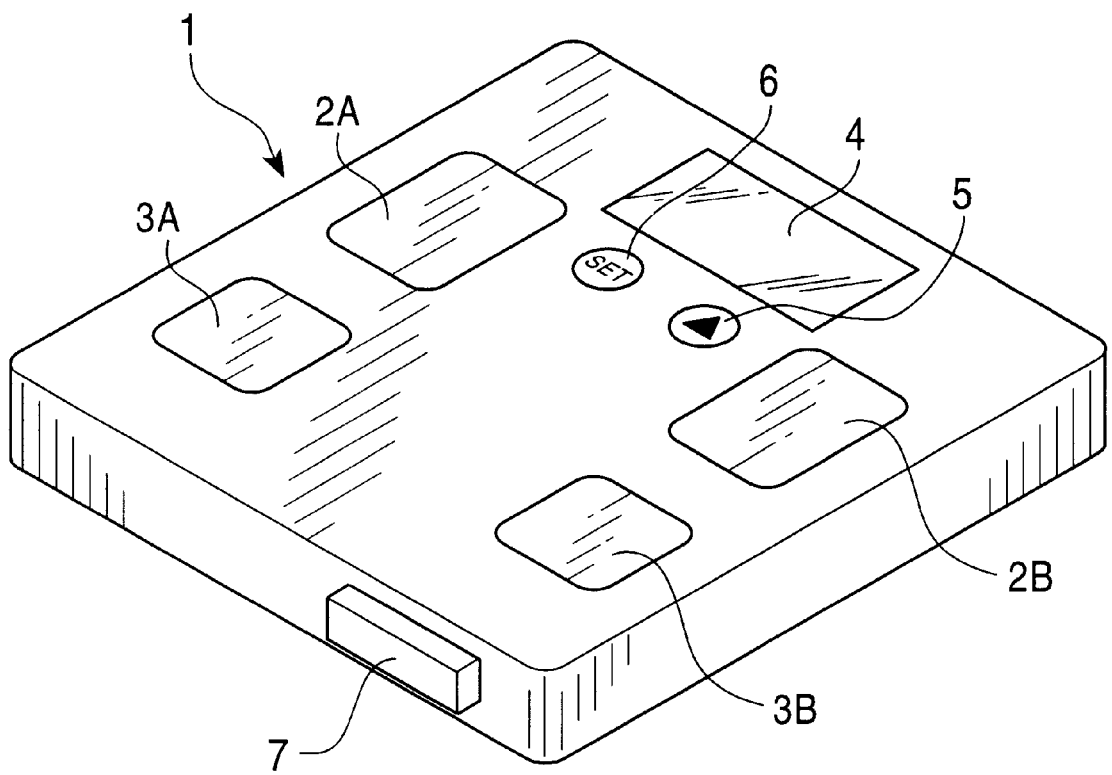
FIG. 2 is a perspective view of a body fat meter according to a first embodiment of the present invention.

FIG. 2 is a perspective view of a body fat meter for measuring a bioelectric impedance between both feet based on the bioelectric impedance method according to a first embodiment of the present invention. The body fat meter 1 has a top surface as a measuring face, and is provided with four electrodes thereon including two current electrodes 2A, 2B and the other two voltage electrodes 3A, 3B, and is further provided with a display section 4 for displaying information related to the measured body fat, and a numeral value change button 5 and a set button 6 for entering personal data of a person to be measured. A measurement start switch 7 to be pressed for body fat measurement is mounted on a front face of the main body. Accordingly, the body fat meter is similar in its external appearance to a conventional body fat meter.

In the initial stage of measurement procedure, a person to be measured presses the numeral value change button 5 and the set button 6 to register one's personal information such as height, weight, sex, age or the like. In the actual stage of measurement of body fat, the body fat meter is actuated for starting measuring operation when the person to be measured presses the measurement start switch 7 and then his or her bare soles are placed thereon so as to come into contact with electrode portions on the measuring face of the body fat meter. At that time the tiptoe and heel of the left foot are brought into contact with the current electrode 2A and the voltage electrode 3A respectively, and so are those of the right foot with the current electrode 2B and the voltage electrode 3B respectively. Thus, there is no particular difference in the usage between a body fat meter of the prior art and that of the present invention.

Figure 3:
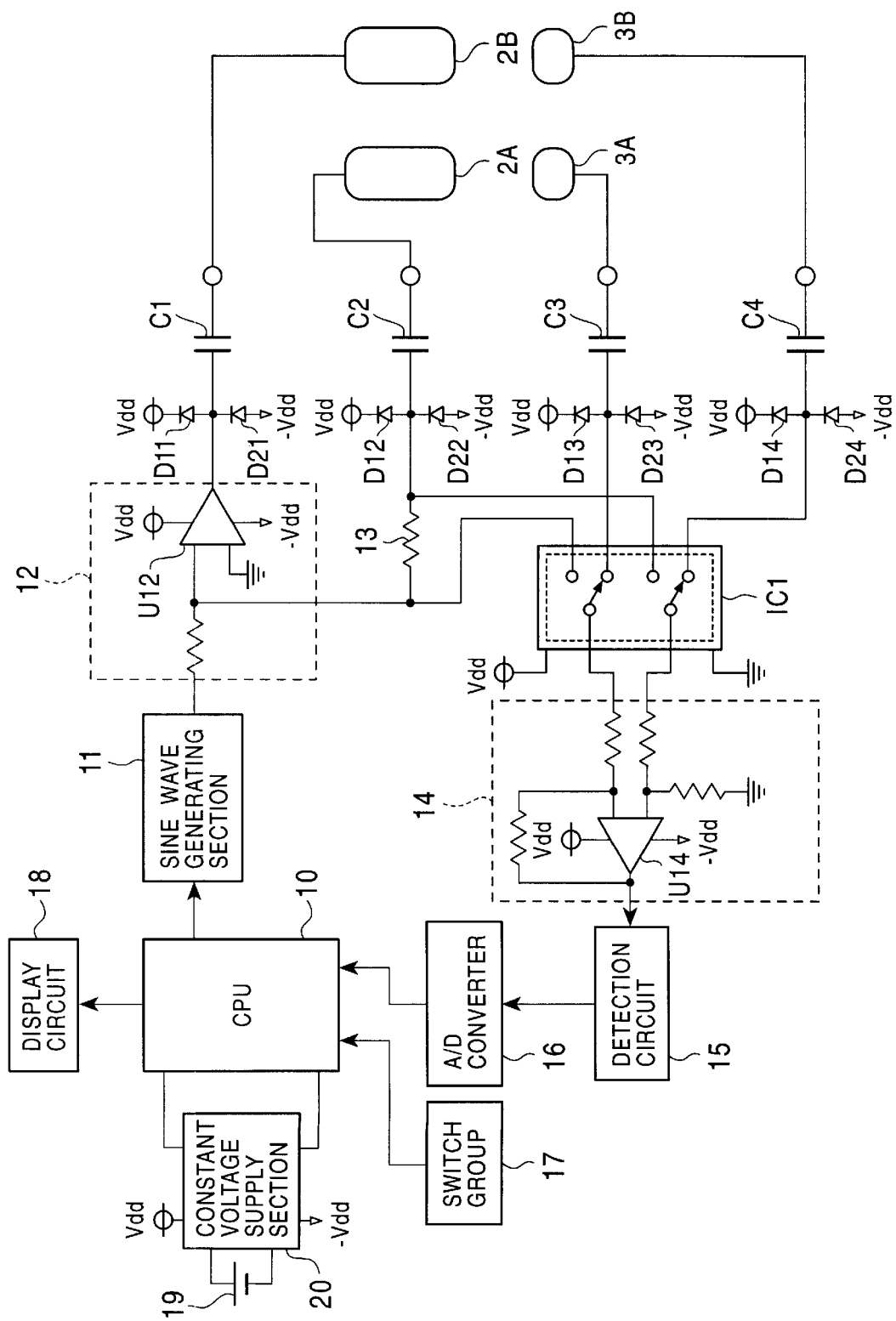
FIG. 3 is a block diagram illustrating an internal measuring circuit of the body fat meter according to the first embodiment of the present invention.

FIG. 3 is a block diagram of a circuit configuration of a body fat meter based on the bioelectric impedance method according to the present invention described above.

An internal measuring circuit of the body fat meter 1 includes a CPU 10 for controlling and processing various operations. This CPU 10 is connected to a sine wave signal generating section 11 for generating an alternating current or a measuring current in response to a processing instruction from the CPU 10, which in turn is connected to a constant current circuit section 12 including a constant current circuit operational amplifier U12 for generating a constant current in response to an output signal from the sine wave signal generating section 11, and this constant current circuit section 12 is connected at one output terminal thereof to the current electrode 2B via a capacitor C1 and also is connected at another output terminal thereof to the other current electrode 2A via a reference resistor 13 and another capacitor C2.

Each of the voltage electrodes 3A and 3B is connected to an analogue switch IC1 via a capacitor C3 or C4 respectively. This analogue switch IC1 is configured such that it may selectively be switched to make connection either to the reference resistor 13 or to a circuit for measuring the body impedance. This reference resistor 13 is installed within a current path of the measuring current to make the measurement of the bioelectric impedance more accurate such that, while applying a current to a certain path including that between both feet of the person, a voltage value determined when the switch IC1 makes a connection to the resistor 13 and another voltage value determined when the analogue switch IC1 is connected to a circuit including both feet of the person are measured and then latter voltage value is compared with the former voltage value which is precisely determined based on the reference resistor. The analogue switch IC1 is connected to a voltage amplifying circuit section 14 including an operational amplifier U14 for amplifying the measured voltage value signal, which in turn is connected to a detection circuit 15 for shaping a voltage waveform, which in turn is connected to an A/D converter 16 for converting a data of shaped voltage waveform from analogue to digital values, and finally the digital value generated by the A/D converter 16 is input into the CPU 10.

A switch group 17 including the numeral value change button 5, the set button 6, and the measurement start switch 7 as shown in FIG. 2 is connected to the CPU 10, and also is connected thereto a display circuit 18 including a display section 4 for displaying information related to body fat such as the body fat rate or the body fat mass which is estimated by combining the determined bioelectric impedance value and personal information stored in advance. Thus, the CPU 10 computes the bioelectric impedance value based on the input current value and the detected voltage value, and then estimates the body fat rate or the body fat mass based on personal information stored in advance and the determined bioelectric impedance value, and finally displays the result on the display section 4.

A battery 19 is connected to a constant voltage supply section 20, where a rated voltage (Vdd) is generated and output for driving the whole measuring circuit, and this constant voltage supply section 20 is connected to respective elements including the CPU 10 to supply a constant voltage. This constant voltage supply section 20 is generally configured by combining a three terminal regulator or the like so as to output the rated voltage (Vdd and −Vdd).

Diodes D11 to D14 and D21 to D24 are provided to prevent possible electrostatic breakage because sometimes several kV of voltage is applied from the electrodes by the static electricity when socks or clothes charged by a carpet or the like come into contact with any of the electrodes 2A, 2B, 3A, 3B. To prevent the circuit breakage by the high voltage, these diodes are provided to discharge the current to Vdd or −Vdd when the high voltage is applied between the electrodes and the measuring circuit and thereby an excessive current is prevented from being applied to the circuits.

Capacitors C1 to C4 are new elements employed in the present invention. First, a case where a circuit element in a circuit without capacitors C1 to C4 has failed will be described.

It is assumed that the diodes D11 and D21 installed against the electrostatic breakage have failed or have already been out of order due to the static electricity when a person places himself on a body fat meter to measure his body fat rate by bringing his soles into contact with respective electrodes 2A, 2B, 3A, 3B. If Vdd and −Vdd are equal to +4V and −4V respectively, a potential difference of 8 volts is applied between 2B and 2A because D11 and D22 are conductive. If the left and right tiptoes are in contact with the 2B and 2A respectively, the potential difference of 8 volts is also applied between the feet of the human body. Since the impedance between both feet of an ordinary adult male is regarded to be about 500 Ω, a direct current of 16 mA is applied between the feet.

$$8(V)/500(\Omega)=16 \text{ (mA)}$$

According to the table shown in FIG. 1, this current of 16 mA is regarded to have a considerable effect on a human body, that is, a considerable pain, though he can escape by himself from the condition caused by the current.

Thus, when an electric component of the measuring circuit is broken or out of order, several volts of potential difference may be produced between electrodes, and if a human body comes into contact with the electrode at this time, a current of several tens mA may possibly be applied to a human body. Similar accident may occur under some conditions not limited to the case of failure in the diode against electrostatic breakage. That is, several volts of potential difference may be generated between electrodes and consequently a condition similar to that described above may occur when, for example, the constant current operational amplifier U12 is broken and the output from the operational amplifier turns to be Vdd or −Vdd, or when the analogue switch IC1 is broken and a conductive state is established inside the circuit between an IC terminal connected to any of the electrode plates and Vdd or the negative pole of the power supply, which may occur when static electricity is applied to the circuit or a certain degree of load is applied to the body fat meter due to an accidental drop thereof. Since the impedance between both feet varies from person to person to be measured and the rated voltages Vdd and −Vdd in the circuit vary depending on design concept, measurement accuracy or the like, the current described above is not always applied to all the persons, but a current exceeding that level may be applied to the human body.

Secondly, a circuit provided with capacitors C1 to C4 will be described.

It is again assumed that the diodes D11 and D21 installed against the electrostatic breakage have failed or have already been out of order due to the static electricity when a person places himself on a body fat meter to measure his body fat rate while bringing his soles into contact with respective electrodes 2A, 2B, 3A, 3B. Though the diodes D11 and D22 are conductive at this time, no direct current passes through the person owing to the capacitors C1, C2 installed in the path even if a person to be measured places himself on the body fat meter while bringing his or her soles into contact with each of the electrodes 2A, 2B. Accordingly, when this capacitor is installed between each electrode and the measuring circuit, such abnormal case can be avoided that a direct current of several tens mA passes through the human body.

Even if the capacitor is installed in the measuring path, no particular trouble comes out since the measuring current for measuring the bioelectric impedance is generally an alternating current of about 50 kHz in frequency and of about 500 μA in ampere and consequently the alternating current can pass through the capacitor during the normal operation.

These capacitors C1 to c4 have no effect on the measuring accuracy so long as the capacitors has 0.1 μF of capacity when the measuring current is 50 kHz in frequency. As for these capacitors C1 to C4, an inexpensive capacitor available in the market such as a ceramic capacitor is enough for it, and further an electrolytic capacitor, a film capacitor, or a chip component such as a pressure membrane chip resistor may also be employed.

Figure 4:
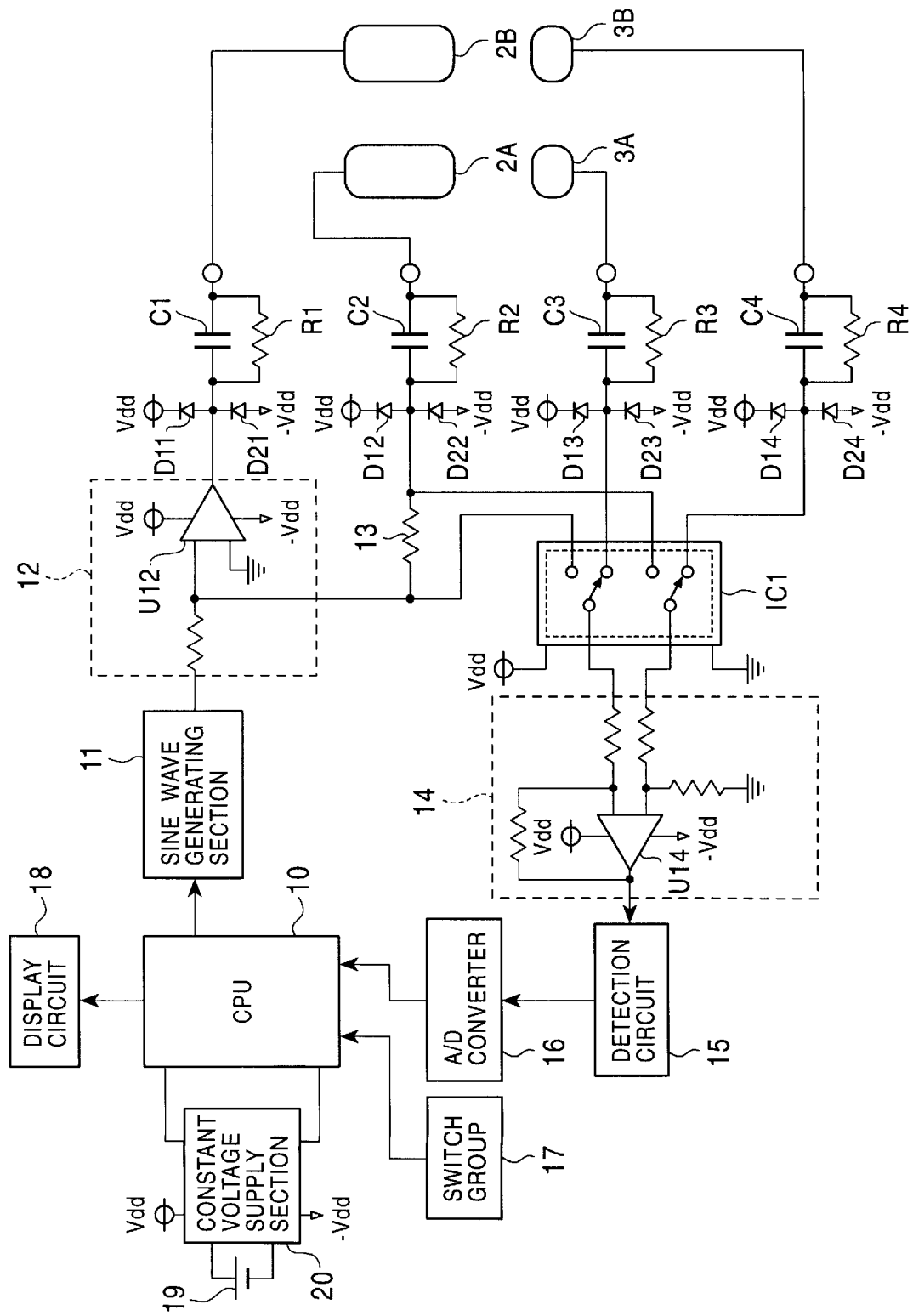
FIG. 4 is a block diagram illustrating an internal measuring circuit of a body fat meter according to a second embodiment of the present invention.
Figure 5:
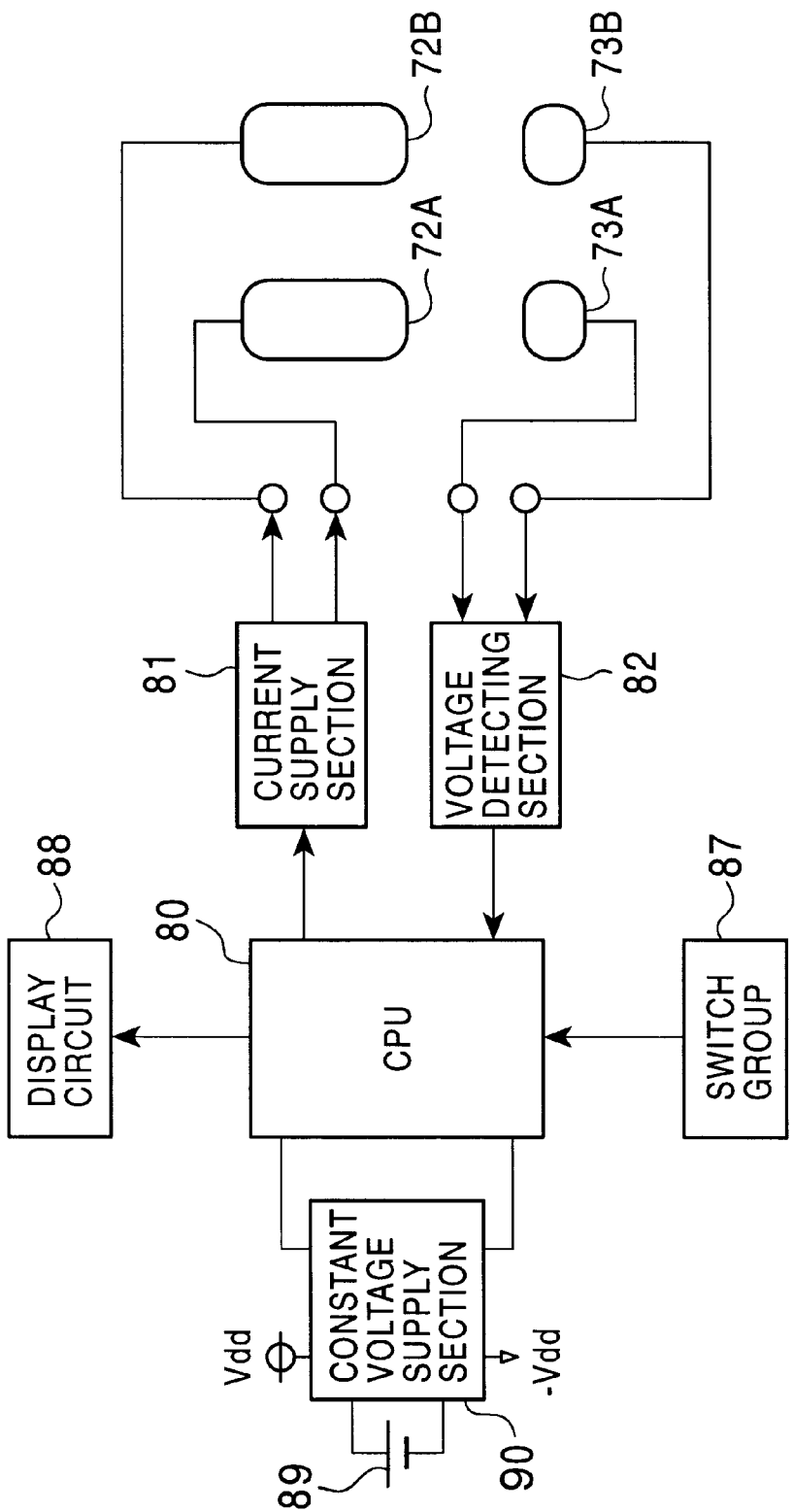
FIG. 5 is a block diagram illustrating an internal measuring circuit of a conventional body fat meter of a prior art.

In the present invention, a resistor may be connected in parallel with the capacitor as shown in a second embodiment of the present invention. FIG. 4 is a block diagram illustrating a circuit configuration of a body fat meter according to the second embodiment, in which each capacitor C1 to C4 is connected in parallel with each resistor R1 to R4 respectively. Each of these resistors has a high resistance of about 1 MΩ.

In case where each capacitor C1 to C4 is installed as in the first embodiment, when a person to be measured comes into contact with the electrode, a small potential difference is produced and a small amount of electric charge may possibly be charged on each capacitor C1 to C4. Though the analogue switch IC1 is configured to be switched to either position to the reference resistor 13 or to the body impedance, the current having been passing through the body to measure the body impedance is charged on the capacitors C1 to C4 when the reference resistor is being measured because the current cannot pass through the measuring circuit. This can be an error factor in the measuring current because of the nature in the circuit. When each resistor R1 to R4 is connected parallel with each capacitor C1 to C4 respectively, the electricity charged on each capacitor can be discharged. Thus connecting a resistor parallel with a capacitor can reduce an error factor and can keep a higher accuracy.

In this second embodiment, as to the circuit components other than the resistors R1 to R4, the same component can be employed and configured to work in the same way as those shown in the first embodiment.

It is again assumed that the diodes D11 and D21 installed against the electrostatic breakage have failed or have already been out of order due to the static electricity when a person places himself on a body fat meter to measure his body fat rate while bringing his soles into contact with respective electrodes 2A, 2B, 3A, 3B. Though the diodes D11 and D22 are conductive at this time, no direct current passes through the person owing to the capacitors C1, C2 installed in the paths even if a person to be measured places himself on the body fat meter while keeping his or her soles in contact with each electrodes 2A, 2B. Further, only a small amount of current passes through the resistors R1, R2. When a voltage of 8 volts is applied and each resistor has a resistance of 1 MΩ, the current path has a resistance of over 2 MΩ including that of human body and accordingly the current passing through the current path can be calculated by the equation below.

8 volts/2 (MΩ)=4 (μA)

The current is only 4 μA. This current causes no trouble even if it passes through the human body because the current is far below the least sensing level according to the table shown in FIG. 1. Accordingly even if a set of a capacitor and a resistor arranged parallel with each other is installed in the measuring circuit, such abnormal case that a direct current of several tens mA passes through the human body can be avoided.

Even if a set of a capacitor and a high resistor arranged parallel with each other is installed in the measuring circuit, no particular trouble comes out during the measurement since the measuring current employed for measuring the bioelectric impedance is generally an alternating current of about 50 kHz in frequency and of about 500 μA in ampere and consequently the alternating current can pass through the capacitor.

As for a circuit element, an inexpensive capacitor and a resistor available in the market such as a ceramic capacitor and a carbon resistor respectively are enough for it.

Further, in the first and second embodiments, the diodes are installed between each electrode and the measuring circuit to prevent the static electricity problem, and a point between each electrode and the connecting point of the diodes is selected to install the capacitor or the set of a capacitor and a resistor. Thus, the static electricity which may cause the circuit failure can be released to Vdd or −Vdd so as not to be discharged from the electrode to the measuring circuit, and further even if the diode might fail, an excessive current is prevented from passing from the electrode to the human body since the capacitor could work.

Though, as to the configuration of the body fat meter, only the case where the bioelectric impedance between both feet is measured thereby has been described, the present invention is not limited thereto but it can be applied to such bioelectric impedance measurement between both hands, between a hand and a foot, or between proper body portions by bringing them into contact with the electrodes.

Further, though the present invention has been described herein as an apparatus for determining the body fat of the person to be measured from the measured bioelectric impedance, the present invention can be applied, without being limited thereto, to an apparatus for measuring various indexes related to body constitution such as total body water volume or fat free mass of a person to be measured.

Further, as to the condition where an excessive current flows, only the case where a diode against static electricity breakage has failed has been described herein, but an unexpected current also passes without being limited thereto when various components have been damaged, and accordingly the configuration of the measuring circuit according to the present invention is not limited thereto.

Further, though a configuration in which a capacitor or a set of a capacitor and a resistor arranged parallel with each other is connected to each electrode has been described herein, the present invention may be configured in any form so long as no direct current passes the current path including a human body, and accordingly the number of capacitors or that of resistors to be installed parallel with a capacitor may properly be changed.

Further, as to providing the capacitor or the set of a capacitor and a resistor arranged parallel with each other, it may be only provided to the current supply electrode but not to the voltage measuring electrode. This is because the circuit for measuring voltage has a high impedance, and therefore current is hardly applied to the living body even when the circuit element has failed, that is, there is little risk that a current large enough to have a substantial effect on a human body may be applied.

Further, the present invention is also applicable to such a case with an increased number of electrodes, for example, the case of eight electrode measuring method in which the bioelectric impedance of respective portions of a living body are measured, and in this case, capacitors or sets of capacitors and resistors, each being arranged parallel with each other, may properly be installed between each of the electrodes and the measuring circuit section.

In a bioelectric impedance measuring apparatus for measuring an index related to body constitution of a person to be measured based on the bioelectric impedance method, if the apparatus is configured such that a capacitor is installed between each electrode and a measuring circuit according to the present invention, it is possible to prevent the abnormal condition that an excessive current passes through the human body in case of failure or damage of a circuit element, by using a simple circuit configuration without decreasing the accuracy in measuring the bioelectric impedance.

Further, in a bioelectric impedance measuring apparatus for measuring an index related to body constitution of a person to be measured based on the bioelectric impedance method, if a set of a capacitor and a resistor arranged parallel with each other is installed between each electrode and a measuring circuit according to the present invention, the electricity charged on the capacitor can be discharged and thereby an error factor can be reduced, that is, the bioelectric impedance can be measured more accurately compared with the case in which only a capacitor without a resistor is employed.

Further, in a bioelectric impedance measuring apparatus, if a capacitor or a set of a capacitor and a resistor arranged parallel with each other is installed in the current supply electrode side and another capacitor or another set of a capacitor and a resistor arranged parallel with each other is optionally installed in the voltage measuring electrode side, a safety countermeasure can be provided always on the current supply electrode side to which a direct current is likely to be applied, and the probability that a current having a substantial effect on a living body passes from each electrode thereto can sufficiently be suppressed because a current is hardly applied from the voltage measuring electrode to the living body owing to the high impedance of the measuring circuit.

Further, in a bioelectric impedance measuring apparatus, if a set of a capacitor and a resistor arranged parallel with each other is installed between each electrode and a measuring circuit, a set of a capacitor and a resistor arranged parallel with each other is installed close to said electrode, and a diode for electrostatic safety countermeasure is installed close to said measuring circuit, a safety countermeasure can be provided to prevent such abnormal condition that an excessive current is applied to a human body when elements in said circuit has failed or broken, by using a simple circuit without decreasing the accuracy in measuring the bioelectric impedance, and the circuit failure caused by static electricity can also be prevented, which reduces risk to the apparatus as well as to the human body.

Further, when a ceramic capacitor is employed as said capacitor, an impedance measuring apparatus equipped with a safety countermeasure can be provided without any substantial increase in cost even if the apparatus employs a plurality of capacitors because of the low unit cost of the ceramic capacitor.

What is claimed is:

1. A bioelectrical impedance measuring apparatus comprising a plurality of electrodes including current electrodes and voltage electrodes for contacting the skin of a person to be measured, an alternating current generating unit connected to said current electrodes so that an alternating current may be flowed into the body of the person, a voltage measuring unit connected to said voltage electrodes so that a voltage between said voltage electrodes may be measured, and a bioelectrical impedance determining unit for determining the bioelectrical impedance of the body of the person on the basis of the alternating current flowed into the body of the person and the measured voltage, said apparatus further comprising a parallel circuit of a capacitor and a resistor between said alternating current generating unit and said current electrodes.

2. A bioelectrical impedance measuring apparatus as defined in claim 1, further comprising a diode for electrostatic safety countermeasure between said alternating current generating unit and said parallel circuit capacitor and resistor.

3. A bioelectrical impedance measuring apparatus comprising a plurality of electrodes including current electrodes and voltage electrodes for contacting the skin of a person to be measured, an alternating current generating unit connected to said current electrodes so that an alternating current may be flowed into the body of the person, a voltage measuring unit connected to said voltage electrodes so that a voltage between said voltage electrodes may be measured, and a bioelectrical impedance determining unit for determining the bioelectrical impedance of the body of the person on the basis of the alternating current flowed into the body of the person and the measured voltage, said apparatus further comprising a parallel circuit of a capacitor and a resistor between said voltage measuring unit and said voltage electrodes.

4. A bioelectrical impedance measuring apparatus as defined in claim 3, further comprising a diode for electrostatic safety countermeasure between said voltage measuring unit and said parallel circuit of capacitor and resistor.

5. A bioelectrical impedance measuring apparatus comprising a plurality of electrodes including current electrodes and voltage electrodes for contacting the skin of a person to be measured, an alternating current generating unit connected to said current electrodes so that an alternating current may be flowed into the body of the person, a voltage measuring unit connected to said voltage electrodes so that a voltage between said voltage electrodes may be measured, and a bioelectrical impedance determining unit for determining the bioelectrical impedance of the body of the person on the basis of the alternating current flowed into the body of the person and the measured voltage, said apparatus further comprising a first parallel circuit of a capacitor and a resistor between said alternating current generating unit and said current electrodes and a second parallel circuit of a capacitor and a resistor between said voltage measuring unit and said voltage electrodes.

6. A bioelectrical impedance measuring apparatus as defined in claim 5, further comprising a diode for electrostatic safety countermeasure between said alternating current generating unit and said first parallel circuit of capacitor and resistor and a diode for electrostatic safety countermeasure between said voltage measuring unit and said second parallel circuit of capacitor and resistor.

7. A bioelectrical impedance measuring apparatus as defined in any one of claims 1 to 6, wherein said electrodes are for contacting the skin of the feet of the person, and said measured bioelectrical impedance is measured between the feet of the person.

* * * * *